United States Patent
Riihimaa

(10) Patent No.: US 12,167,722 B2
(45) Date of Patent: Dec. 17, 2024

(54) APPARATUS FOR GROWING INVERTEBRATES

(71) Applicant: Entoprot OY, Oulu (FI)

(72) Inventor: Ari Riihimaa, Oulu (FI)

(73) Assignee: Entoprot OY, Oulu (FI)

( * ) Notice: Subject to any disclaimer, the term of this patent is extended or adjusted under 35 U.S.C. 154(b) by 203 days.

(21) Appl. No.: 17/778,139

(22) PCT Filed: Nov. 19, 2020

(86) PCT No.: PCT/FI2020/000016
§ 371 (c)(1),
(2) Date: May 19, 2022

(87) PCT Pub. No.: WO2021/099674
PCT Pub. Date: May 27, 2021

(65) Prior Publication Data
US 2022/0408706 A1    Dec. 29, 2022

(30) Foreign Application Priority Data
Nov. 21, 2019    (FI) .................................. 20195997

(51) Int. Cl.
*A01K 67/033* (2006.01)
*A01K 1/00* (2006.01)

(52) U.S. Cl.
CPC .............. *A01K 67/033* (2013.01); *A01K 1/00* (2013.01)

(58) Field of Classification Search
CPC ................. A01K 80/00; A01K 67/03
See application file for complete search history.

(56) References Cited

U.S. PATENT DOCUMENTS

2015/0296760 A1* 10/2015 Perednia .............. A01K 67/033

FOREIGN PATENT DOCUMENTS

| CN | 208692094 U | 4/2019 | |
| KR | 20190073891 A | 6/2019 | |
| WO | WO 96/31117 | * 10/1996 | ............. A01K 80/00 |
| WO | WO2017198895 A1 | 11/2017 | |
| WO | WO2018169398 A1 | 9/2018 | |
| WO | WO2019211511 A1 | 11/2019 | |

OTHER PUBLICATIONS

English language machine translation of CN208692094U.
English language machine translation of KR20190073891A.
Search Report from the Finnish Patent Office for 20195997.
Written Opinion for PCT/FI2020/000016.

* cited by examiner

*Primary Examiner* — Joshua J Michener
*Assistant Examiner* — Henry Hooper Mudd
(74) *Attorney, Agent, or Firm* — BelayIP

(57) ABSTRACT

An apparatus for growing invertebrates, such as arthropods, rheumatoid worms and nematodes is described. The apparatus includes a rotatable casing defining a chamber and at least one growing platform inside said casing. Inside the casing there is a group of first pipes having a pipe wall. The first pipes are configured to act as growing platforms providing growing spaces for the invertebrates. Preferably the number of first pipes is more than three. The first pipes may be immovably attached to the casing.

15 Claims, 3 Drawing Sheets

APPARATUS FOR GROWING INVERTEBRATES

CROSS REFERENCE TO RELATED APPLICATIONS

This application is a national phase application of International Application No.: PCT/FI2020/000016, filed on Nov. 19, 2020, and claims the benefit of priority of Finnish application 20195997, filed on Nov. 21, 2019, the content of both of which is herein incorporated by reference.

BACKGROUND OF THE INVENTION

Field of the Invention

The invention relates to an apparatus for growing invertebrates, said apparatus comprising a rotatable casing defining a chamber and at least one growing platform inside said casing.

Description of Related Art

Invertebrates, such as insect larvae and worms, can be used as a protein source for animals and humans. Invertebrates can be grown efficiently in artificial growing spaces by placing them in contact with a suitable food source. When the invertebrates have grown enough, they are removed from the growing space and processed into animal or human food. Invertebrates can use a wide range of organic material as food, which makes them ideal for protein production. However, attempts to produce invertebrates in industrial scale are still rare.

A conventional method for growing invertebrates is to use flat trays as growing platforms. Food is added periodically to the surface of the trays. Keeping an optimum amount of food on the trays is difficult. The trays should carry a thick layer of food to feed as many larvae as possible. On the other hand, if the thickness of the food layer is too big, the heat inside the food layer may rise too high and the amount of oxygen inside the food layer may fall too low for the invertebrates to grow. This increases the risk of undergoing anaerobic fermentation.

Document US 2015/0296760 A1 discloses a rotating feeder bin for growing, feeding and harvesting insect larvae. The feeder bin has a cylindrical sidewall. The inside surface of the bin may be lined with mixing bars or ridges, whose function is to mix and aerate the contents of the bin, when the bin is rotated. This feeder bin has no platforms or trays for the food, whereby the bin can offer only a limited growing area for the larvae.

Document FI20187064 discloses an apparatus for growing invertebrates comprising a rotatable casing defining a growing chamber and at least one plate-like growing platform inside the casing. The growing platform is configured to stay in horizontal position, when the casing is rotated. Although the apparatus disclosed in FI20187064 is as such workable, optimal administration of food on the growing platforms is still difficult.

An object of the invention is to provide an apparatus for growing invertebrates in which defects relating to the prior art are diminished.

The object of the invention is achieved with an apparatus, that is characterized in what is disclosed in the independent claim. Some preferred embodiments of the apparatus are disclosed in the dependent claims.

BRIEF SUMMARY OF THE INVENTION

The present invention relates to an apparatus for growing invertebrates, said apparatus comprising a rotatable casing defining a chamber and at least one growing platform inside said casing. Inside the casing there is a group of first pipes having a pipe wall. The first pipes are configured to act as growing platforms providing growing spaces for the invertebrates. The pipe walls of the first pipes have first openings for feeding nutrient inside the first pipe through the first openings. The number of first pipes depends on the volume and dimensions of the casing and it can be chosen. Preferably the number of first pipes is more than three.

The apparatus according to the invention is especially suitable growing space for invertebrates that use spiracles and tracheae for gas exchange, i.e. they need air, but it is applicable to other kinds of invertebrates too. By expression 'needing air' it is here meant that the invertebrates breathe gas. Invertebrate groups that are capable to grow in the apparatus according to the invention, but are not limited to these, are arthropods, rheumatoid worms and nematodes. Word 'grow' is not to be understood to mean the whole life span of the invertebrates, but it can include only one or more life stages of parts of them. An example of a life stage is the larval stage of a fly.

In a first preferred embodiment of the apparatus according to the invention the first pipes are arranged into the casing immovably. Immovably arrangement means, that when the casing rotates around its rotation axis, the position and location of the first pipes in relation to the casing remains unchanged, i.e. the first pipes rotate around the rotation axis of the casing and turn simultaneously around their own rotation axis.

In a second preferred embodiment of the apparatus according to the invention the casing comprises a first end wall, a second end wall and a cylindrical side wall. The first pipes have a first end attached to the first end wall and a second end attached to the second end wall.

In yet another preferred embodiment of the apparatus according to the invention in connection at least one first opening there is a scoop for directing nutrient towards the first opening.

In yet another preferred embodiment of the apparatus according to the invention inside at least one first pipe there is a second pipe, which second pipe has a pipe wall, which second pipe is configured to act as growing platform and/or growing space for the invertebrates. Preferably, the pipe wall of the second pipe has second openings for feeding nutrient inside the second pipe through the second openings.

In yet another preferred embodiment of the apparatus according to the invention the second pipe is movable in relation to the first pipe and the first pipe and the second pipe inside said first pipe can be arranged to a first formation, where at least most of each first opening is substantially aligned with one second opening and to a second formation, where at least most of the first openings are not aligned with any second opening. Preferably, substantially all first openings of the first pipe are aligned with one second opening of the second pipe, when the first and second pipes are in the first formation and substantially none of the first openings is aligned with any second opening, when the first and second pipes are in the second formation. Preferably, the first and second openings are substantially equal in size and shape. This means, that a first opening can be aligned with only one second opening at the time.

In yet another preferred embodiment of the apparatus according to the invention the second pipe is movable inside the first pipe in the axial direction of the first pipe. Alternatively or additionally the second pipe is rotatable inside the first pipe.

In yet another preferred embodiment of the apparatus according to the invention the attachment point of the first end of the first pipe to the first end wall and the attachment point of the second end of the first pipe to the second end wall are different seen in the radial direction from the imaginary central axis of the casing. In this embodiment the first ends of the first and second pipes dive into the nutrient layer and rise out of the nutrient layer first, i.e. before the second end of the pipes, during the rotation of the casing. The nutrient enters inside the first and second pipes through the first and second openings in the first end of the pipes and flow inside the pipes towards the second end as the casing rotates.

In yet another preferred embodiment of the apparatus according to the invention the first pipe and the second pipe are curved. Preferably, the distance between the outer surface of the first pipe and the inner surface of the casings side wall stays constant over the whole length of the first pipe. The first pipe may have spiral or helical form.

In yet another preferred embodiment of the apparatus according to the invention it further comprises a support frame supporting the casing and a motor for rotating the casing around a rotation axis.

In yet another preferred embodiment of the apparatus according to the invention it further comprises a central pipe having a chamber portion locating inside the casing and a first end extending outside the casing. The chamber portion has apertures for feeding nutrient inside the casing via the central pipe. Preferably, the imaginary central axis of the central pipe is coaxial with the rotation axis of the casing.

In yet another preferred embodiment of the apparatus according to the invention the first end wall or the second end wall is openable.

In yet another preferred embodiment of the apparatus according to the invention the casing has holes for feeding air inside the casing and at least one openable hatch for removing invertebrates from the casing. Preferably, the holes and the hatches are arranged to the first and/or to the second end wall.

In yet another preferred embodiment of the apparatus according to the invention the casing is substantially watertight. Substantially watertight casing enables using organic material containing slurry as a nutrient for the invertebrates.

An advantage of the invention is, that it increases the amount of the invertebrates that can grow in a certain volume of a growing chamber compared to the prior art methods. Thus, the invention makes it possible to use the floor area or 3-dimensional space of the production facility more efficiently.

A further advantage of the invention is that it provides an efficient way to mix the food inside the growing chamber and at the same time provides an undisturbed area for the invertebrates to feed and grow.

Another further advantage of the invention is that it improves the growing process by providing the invertebrates a constant and steady growing environment. The invention makes it easier to arrange the measurement and adjustment of various environmental variables such as temperature and concentrations of chemical substances and gasses. Also heat-control and washing the growing chamber and its contents are easier.

Another further advantage is that the invention can easily be modified for different species of invertebrates that require different growing conditions. The invention also prevents the invertebrates from drowning in the food.

Another further advantage of the invention is, that it prevents the formation of anaerobic areas in the food layer and reduces the risk of an anaerobic fermentation.

BRIEF DESCRIPTION OF THE SEVERAL VIEWS OF THE DRAWING

Further advantages, features, and details of the various embodiments of this disclosure will become apparent from the ensuing description of a preferred exemplary embodiment and with the aid of the drawings. The features and combinations of features recited below in the description, as well as the features and feature combination shown after that in the drawing description or in the drawings alone, may be used not only in the particular combination recited, but also in other combinations on their own, without departing from the scope of the disclosure.

In the following the invention will be described in detail, by way of examples, with reference to the accompanying drawings in which.

DETAILED DESCRIPTION OF THE INVENTION

As used throughout the present disclosure, unless specifically stated otherwise, the term "or" encompasses all possible combinations, except where infeasible. For example, the expression "A or B" shall mean A alone, B alone, or A and B together. If it is stated that a component includes "A, B, or C", then, unless specifically stated otherwise or infeasible, the component may include A, or B, or C, or A and B, or A and C, or B and C, or A and B and C. Expressions such as "at least one of" do not necessarily modify an entirety of the following list and do not necessarily modify each member of the list, such that "at least one of "A, B, and C" should be understood as including only one of A, only one of B, only one of C, or any combination of A, B, and C.

The embodiments in the following description are given as examples only and a person skilled in the art can carry out the invention also in some other way than what is described in the description. Though the description may refer to a certain embodiment or embodiments, this does not mean that the reference would be directed towards only one described embodiment or that the described characteristic would be usable only in one described embodiment. The individual characteristics of two or more embodiments may be combined and new embodiments of the invention may thus be provided.

Figure 1A:
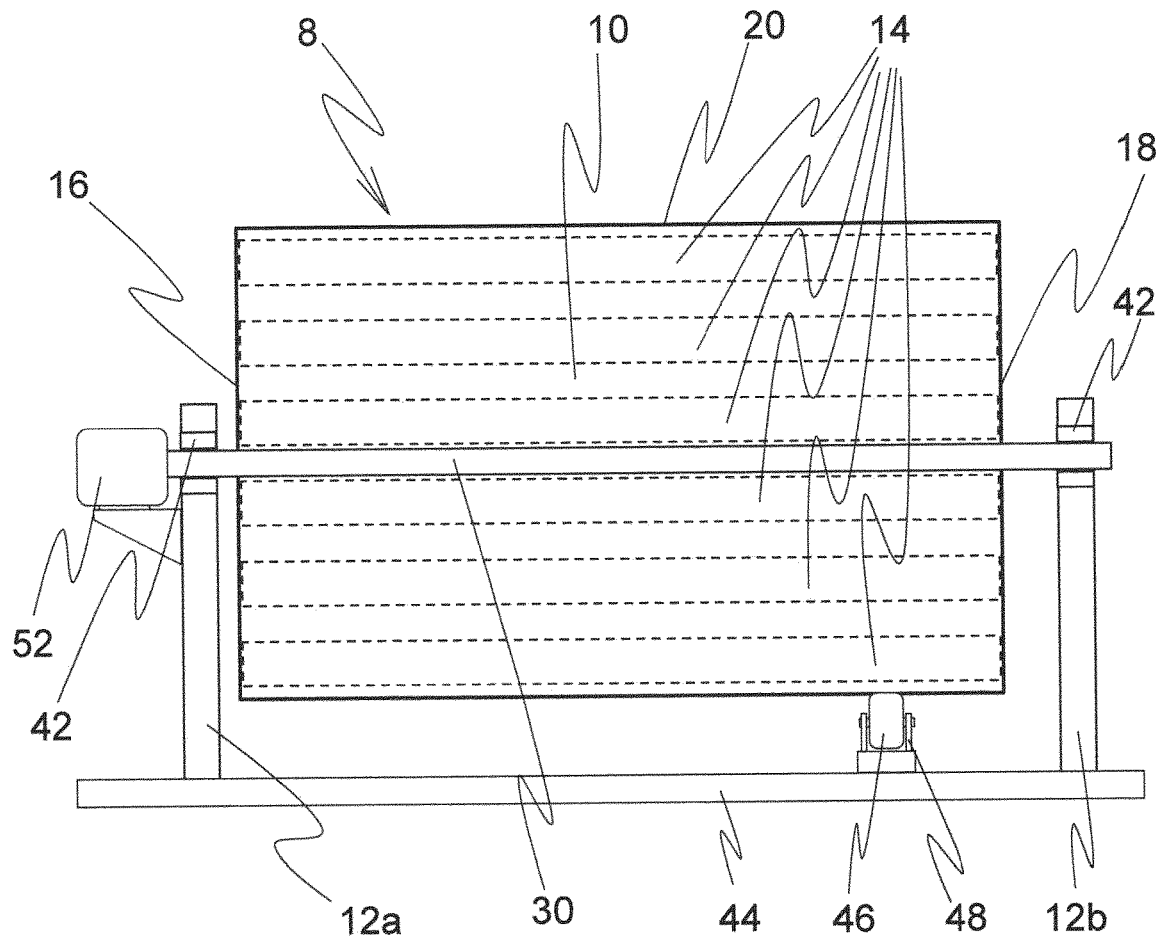
FIG. 1a shows an example of an apparatus according to the invention as side elevation.
Figure 1B:
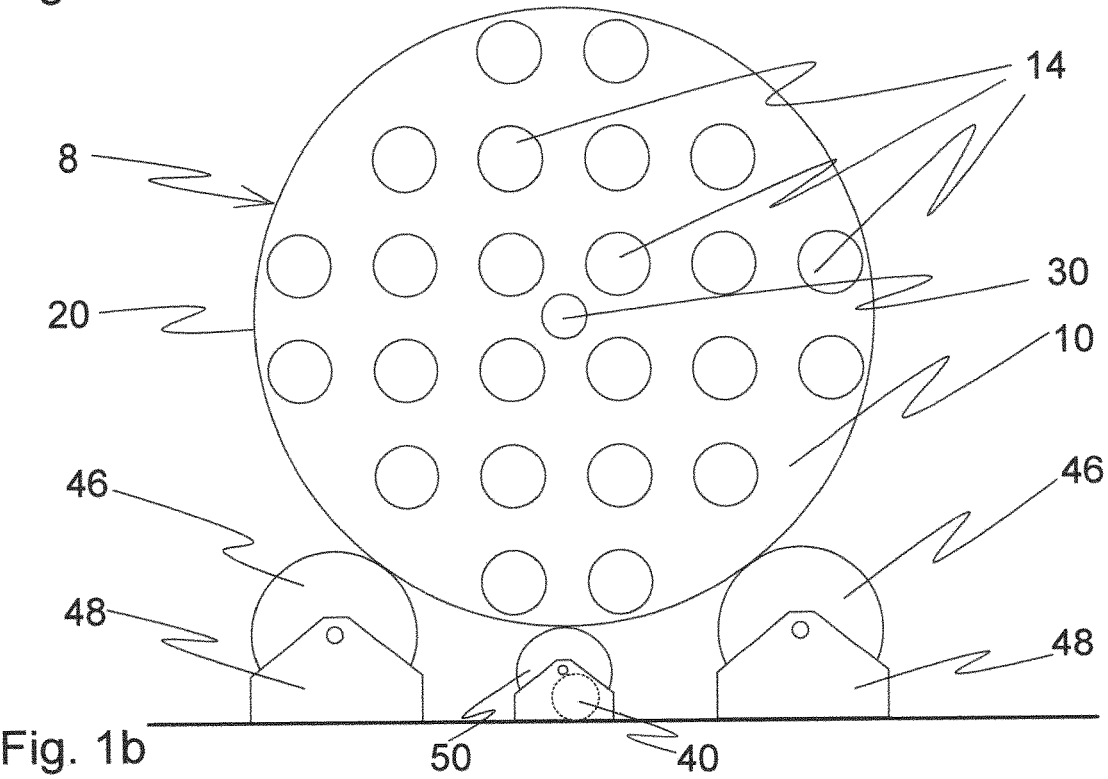
FIG. 1b shows a transverse cross section of the apparatus of FIG. 1a, FIGS. 2a and 2b show a part of the casing belonging to the apparatus of FIG. 1a in a longitudinal cross section view.

In FIG. 1a an example of an apparatus according to the invention is shown as a side elevation and in FIG. 1b the apparatus of FIG. 1a is shown as a transverse cross-sectional view. In the following both figures are explained simultaneously.

The apparatus comprises a casing 8 defining a closed chamber 10, which acts as a growing space for the invertebrates. The casing has a first end wall 16, a second end wall 18 a and cylindrical side wall 20 connecting the side walls. A central pipe 30 goes through the centre points of both end walls. The first end on the central pipe is supported to a first column 12a next to the first end wall outside the chamber and the second end of the central pipe 30 is supported to a second column 12b next to the second end wall 18 outside the chamber. In the upper end of the columns there is a hole, through which the central pipe protrudes. The holes are furnished with bearings 42, which enables the central pipe and the casing 8 attached to it to rotate around the imaginary central axis of the central pipe. Thus, the rotation axis of the casing is coaxial with the imaginary central axis of the central pipe. Preferably, the casing and the central pipe are made of metal.

The lower ends of the columns abut against a load bearing base 44 or a floor. Between the base and the side wall 20 of the casing, near the second end wall there is two support rolls 46 at a distance from each other. Both support rolls are rotatably connected to a bracket 48 resting on the base 44. The first and second columns 12a, 12b, the support rolls and the brackets belong to a support frame, which supports the casing 8 above the base enabling the rotation of the casing. Since the second end of the casing is supported by the support rolls, the load carried by the second column can be small. The primary function of the second column is to support the casing in horizontal direction, when the casing is rotated. Between the support rolls there is a drive wheel 50, which is driven by a motor 40 (FIG. 1b). The outer surface of the drive wheel is pressed against the outer surface of the casing. When the drive wheel is rotated by operating the motor, the casing 8 rotates around its rotation axis.

On the first end on the central pipe 30 there is a pump 52 for pumping nutrient, i.e. food, inside the central pipe. The portion of the central pipe, which is here called the chamber portion, has apertures in the pipe wall (not show in FIGS. 1a and 1b), through which apertures the nutrient flows inside the chamber. The pump may be equipped with a hopper for feeding nutrient into the pump. The nutrient is preferably in a form of organic slurry, which is easily transferable by pumping.

Inside the casing 8 there is a group on first pipes 14, which act as growing surfaces and growing spaces for the invertebrates. The first pipes are attached from the first ends to the first end wall 16 and from their second ends to the second end wall 18. The first pipes are attached to the casing in an immovably manner, i.e. the location and position on the first piper in relation to the casing remains unchanged as the casing rotates around its rotation axis.

Figure 2A:
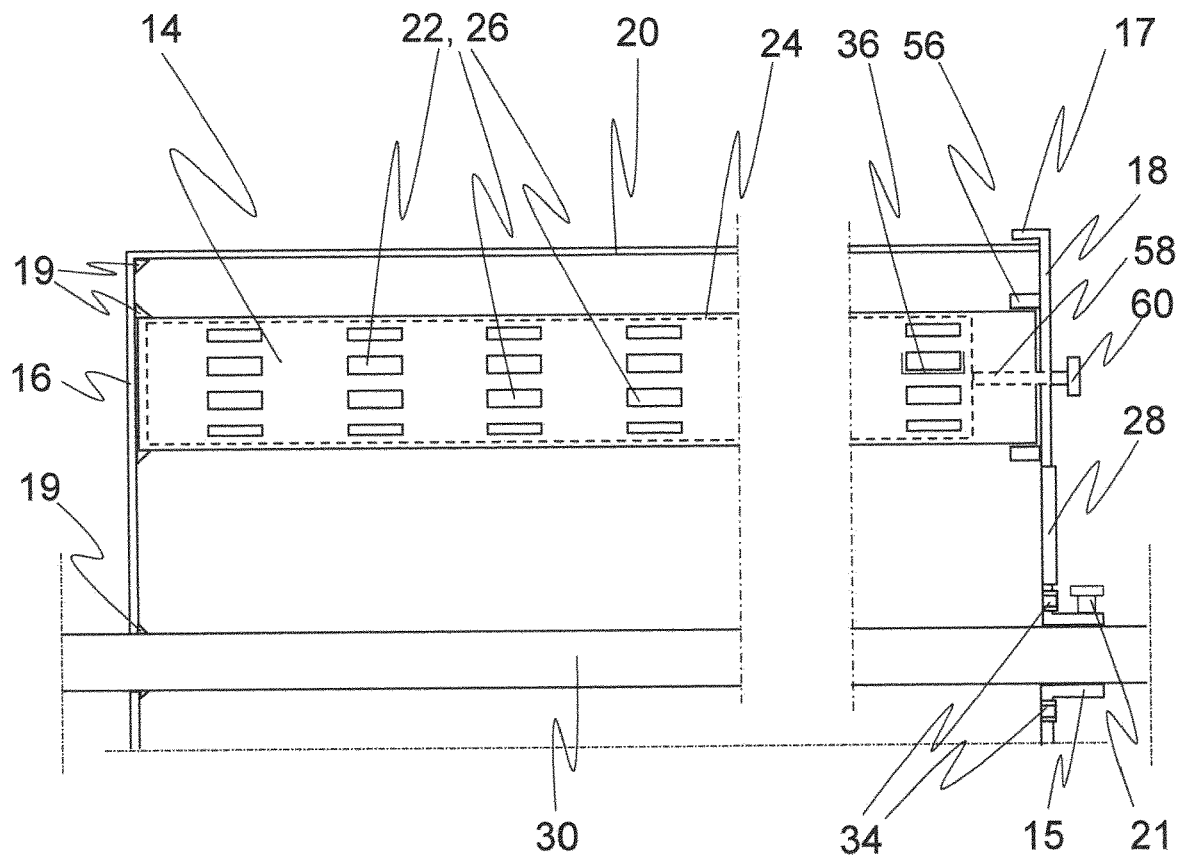
Figure 2B:
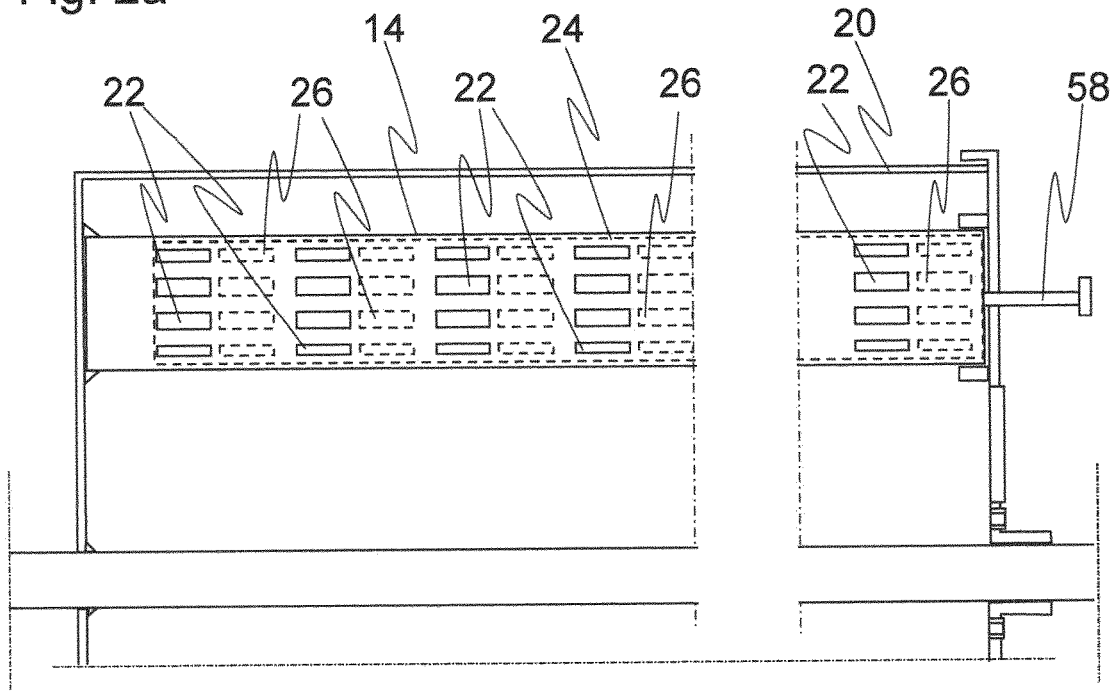

In FIGS. 2a and 2b a part of the casing 8 belonging to the apparatus of FIG. 1a is shown in a longitudinal cross section view. In the following both figures are explained simultaneously.

The casing 8 has a first end wall 16, a second end wall 18 and a cylindrical side wall 20. The first end wall is attached to the side wall and to the central pipe 30 by weld seam 19. The first end wall and the side wall are thus fixedly connected. The second end wall 18 is attached to the second end of the side wall in a detachable manner, i.e., the second end wall is openable. On the edge of the second end wall 18 there is a rim 17 encircling the second end on the side wall 20. In the centre of the second end wall 18 there is a hole surrounded by a tubular sleeve 15. The central pipe 30 goes through the hole and the sleeve. The sleeve is attached to the central pipe with detachable clamping means, such as a clamping screw 21. When the sleeve is connected to the central pipe, the rim secures the joint of the second end of the side wall 20 and the second end wall 18. When the clamping screw is opened, the second end wall may be removed by sliding it towards the second end on the central pipe. The second end wall 18 further comprises holes 34 for feeding air inside the casing 8 and at least one openable hatch 28 for removing invertebrates from the casing.

Inside the casing there is a group of first pipes 14, which have a cylindrical pipe wall. In FIGS. 2a and 2b only one first pipe is depicted to preserve the clarity of the figures. First pipes extend from the first end wall 16 of the casing to the second end wall 18 of the casing. In this embodiment the first pipes are horizontal. The first pipes are attached to the casing in an immovable manner, which means, that the first pipes cannot move or change position in relation to the casing, when the casing rotates around its rotation axis. In the embodiment shown in FIGS. 2a and 2a the immovable attachment has been carried out by joining the first end of the first pipe and the first end wall 16 together by a weld seam 19. The second end wall 18 is provided with a round collar 56, which surrounds the second end on the first pipe 14. When the second end wall is secured in place, the collar prevents the movement of the second end of the first pipe along the surface on the second end wall.

The pipe wall of the first pipe 14 has slit-like first openings 22, through which nutrient and invertebrates can enter inside the first pipe. The first openings are distributed in groups along the whole length of the first pipe. Between each consecutive group there is a portion of solid pipe wall and in each group the openings are evenly distributed around the circumference of the first pipe. On the outer surface of the first pipe 14, in connection of at least one first opening, there may be a scoop 36, which directs nutrient through the first openings. The scoop fills up when the first pipe rotates downwards towards its lowermost position and empties through the first opening when the first pipe rises upwards during the rotation circle of the casing.

Inside at least one first pipe 15 there is a second pipe 24. The length of the second pipe is smaller than the length of the first pipe. The outer diameter of the second pipe is only slightly smaller than the inner diameter of the first pipe, i.e. between the outer surface of the second pipe and inner surface of the first pipe there is a small gap, which enables the second pipe to move inside the first pipe in the longitudinal direction of the pipes. In the pipe wall of the second pipe there are second openings 26 through which nutrient and invertebrates can enter inside the second pipe. The size and shape of the second openings is equal with the size and shape of the first openings and the second openings are distributed over the length and circumference of the second pipe in a similar way than the first openings. Preferably the width of the first and second openings is more than 6 mm and less than the diameter of the pipe.

In the second end of the second pipe 24 there is a rod 58, which penetrates through the second end wall 18 via a hole. The protruding end of the rod is furnished with a detachable handle 60. The second pipe can be moved inside the first pipe by pushing or pulling the handle in the longitudinal direction of the second pipe. In FIG. 2a the second pipe is in the furthermost position at first end on the first pipe and each first opening of the first pipe is in aligned with one second opening of the second pipe. This set-up of the first and second pipe is here called the first formation. In the first formation the first and second openings provide an entrance for the nutrient and the invertebrates through the pipe walls on first and second pipe inside the second pipe. Preferably, the first and second pipes are made of metal.

In FIG. 2b the second pipe is in the furthermost position at second end on the first pipe where each first opening of the first pipe is facing a solid pipe wall portion of the second pipe and each second opening of the second pipe is facing a solid pipe wall portion of the first pipe, respectively. This set-up of the first and second pipe is here called the second formation. When the pipes are in the second formation there is no entrance inside the first and second pipe. The pipes are meant to be settled to the second formation, when there is enough nutrient and invertebrates inside the second pipe, whereby the pipes offer a steady and constant environment for the invertebrates to grow. When the casing rotates, the first and second pipes also rotate around the common centre line of first and second pipe causing the nutrient inside the second pipe to roll over the inner surface of the second pipe. The nutrient is thus in a constant slow movement, which enhances the mixing of air to the nutrient, equalizes the temperature distribution inside the nutrient and prevents the formation of anaerobic areas in the nutrient layer. The outer surface of the first pipe also carries a layer of nutrient and acts as a growing platform for the invertebrates.

In the embodiment depicted in FIGS. 2a and 2b, the second pipe is moved inside the first pipe in the longitudinal direction of the pipes, when the pipes are moved from the first formation to the second formation and vice versa. The second pipe can also be rotated around its rotation axis inside the first pipe whereby the pipes are moved from the first formation to the second formation and vice versa by rotating the second pipe. The rod 58 may be furnished with an actuator for moving and/or rotating the second pipe inside the first pipe.

Preferably there is one second pipe in each first pipe of the apparatus. However, it is also possible that there is a second pipe in only some of the first pipes. Further it is conceivable, that there is no second pipe in any of the first pipes. In the latter case the first pipes alone act as growing spaces for the invertebrates.

Figure 3A:
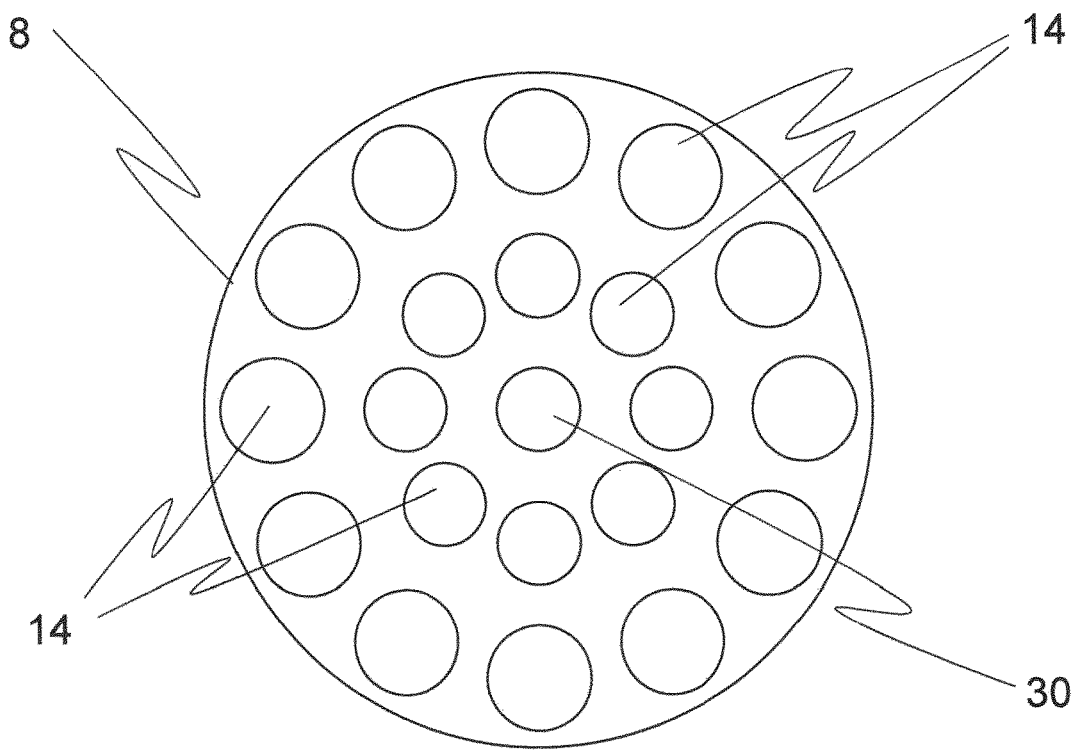
FIG. 3a shows a transverse cross section of the casing of a preferred embodiment of the apparatus according to the invention.
Figure 3B:
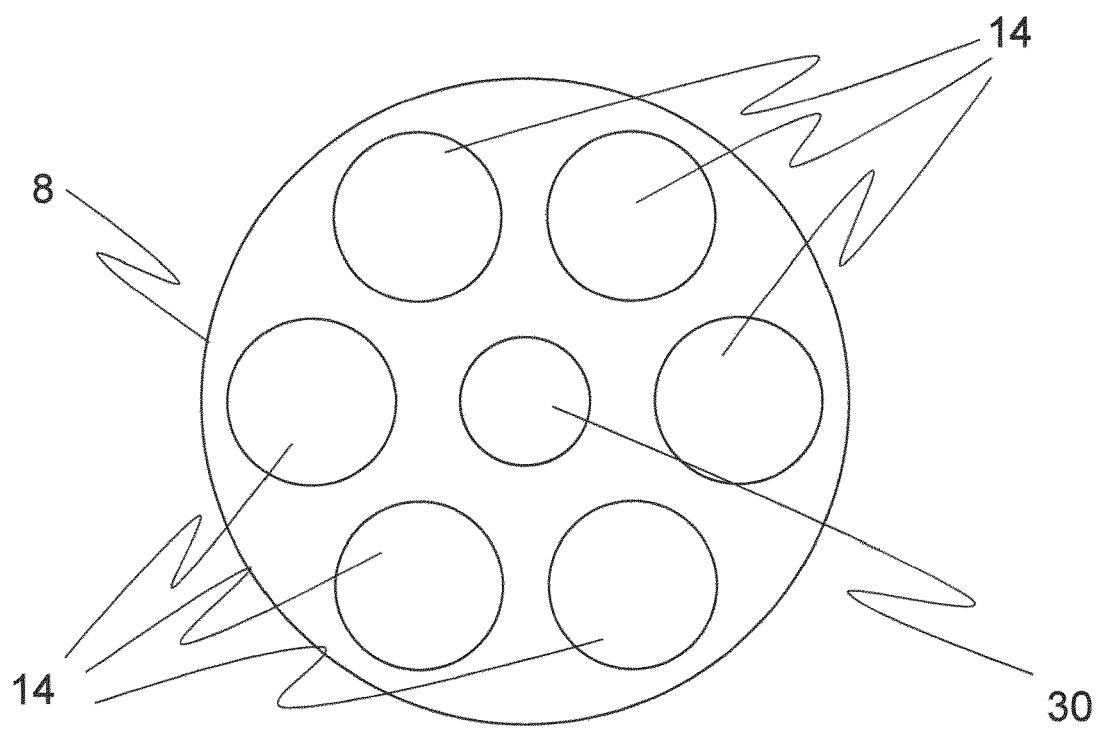
FIG. 3b shows a transverse cross section of the casing of another preferred embodiment of the apparatus according to the invention.

In FIG. 3a a first preferred embodiment the apparatus according to the invention is shown as a transverse cross section and in 3b a second preferred embodiment of the apparatus according to the invention is shown as a transverse cross section. The first pipes can be arranged inside the casing 8 in numerous ways. In the embodiment shown in 3a the first pipes 14 are in two ring-like formations around the central pipe 30. The diameter of the first pipes in the outer ring is bigger that the diameter of the first pipes in the inner ring. Naturally the diameters of the second pipes inside the first pipes follows the diameters of the first pipes. In the embodiment shown in FIG. 3b the first pipes are in one ring-like formation around the central pipe 30. The diameter and number of the first and second pipes can thus be selected and the location inside the casing may be varied. The diameter of the first and second pipes may be 6 mm to 400 mm. Preferably the diameter of the pipes is 50 to 100 mm.

In the embodiments of the invention depicted above, the first pipes are attached to the end walls of the casing. However, it is not necessary to attach or connect the first pipes into the casing side wall or end walls at all. Instead it is possible to fill the interior of the casing, i.e. the chamber, with loose first pipes, which abut against the side wall of the casing and neighbouring pipes. In this embodiment the tight fitting of the first pipes into the casing prevents the first pipes moving inside the casing. The first pipes may be grouped and/or joined together to one or more pipe units outside the casing, which unit/units can be installed to and removed from the casing as a separate part/parts.

Some preferred embodiments of apparatus according to the invention have been disclosed above. The invention is not limited to the solutions explained above, but the inventional idea can be applied in different ways within the limits set by the claims.

The invention claimed is:

1. An apparatus for growing invertebrates, comprising:
a rotatable casing comprising a chamber and at least one growing platform inside said rotatable casing (8),
a group of first pipes arranged inside the casing, wherein:
each of the group of first pipes comprises a pipe wall having first openings configured to feed nutrient inside each of the group of first pipes through the first openings;
each of the group of first pipes is configured to act as growing platforms providing growing spaces for the invertebrates, and
wherein arranged inside at least one of the first pipes is a second pipe comprising a pipe wall and is configured to act as a growing space for the invertebrates.

2. The apparatus according to claim 1, wherein the first pipes are arranged into the casing immovably.

3. The apparatus according to claim 1, wherein the rotatable casing further comprises:
a first end wall,
a second end wall, and
a cylindrical side wall, and
wherein the first pipes further comprise a first end attached to the first end wall and a second end attached to the second end wall.

4. The apparatus according to claim 1, wherein in connection with at least one first opening there is a scoop for directing nutrient towards the first opening.

5. The apparatus according to claim 1, wherein the pipe wall of the second pipe further comprises second openings configured for feeding nutrient inside the second pipe through the second openings.

6. The apparatus according to claim 1, wherein the second pipe is configured to move in relation to the first pipe and the first pipe and the second pipe arranged inside said first pipe is arranged at a first formation where at least a majority of a number of each first opening is substantially aligned with one second opening and at a second formation, where at least a majority of a number of the first openings are not aligned with any second opening.

7. The apparatus according to claim 1, wherein the second pipe is configured to move inside the first pipe in an axial direction of the first pipe.

8. The apparatus according to claim 1, wherein the second pipe is configured to rotate inside the first pipe.

9. The apparatus according to claim 3, wherein the first end further comprises an attachment point to the first end wall, the second end comprises an attachment point to the second end wall, and the attachment point of the second end is different to the first end attachment point from a perspective in a radial direction from an imaginary central axis of the casing.

10. The apparatus according to claim 1, wherein the first pipes and the second pipes are curved.

11. The apparatus according to claim 1, further comprising a support frame supporting the casing and a motor for rotating the casing around a rotation axis.

12. The apparatus according to claim 1, further comprising a central pipe having a chamber portion located inside the casing and a first end extending outside the casing, and wherein the chamber portion comprises apertures configured to feed nutrient inside the casing via the central pipe.

13. The apparatus according to any claim 3, wherein the first end wall or the second end wall is openable.

14. The apparatus according to claim 1, wherein the casing further comprises:
   holes configured to feed air inside the casing, and
   at least one openable hatch configured for removing invertebrates from the casing.

15. The apparatus according to claim 1, wherein the casing is substantially watertight.

* * * * *